(12) United States Patent
Horan et al.

(10) Patent No.: US 6,768,021 B2
(45) Date of Patent: *Jul. 27, 2004

(54) PROCESS IMPROVEMENT FOR CONTINUOUS ETHYL ACETATE PRODUCTION

(75) Inventors: Kimberly Ann Horan, Lewisville, TX (US); Carl David Murphy, Corpus Christi, TX (US); Russell Mark Stephens, Amarillo, TX (US); R. Jay Warner, Corpus Christi, TX (US); Kenneth Allen Windhorst, Pampa, TX (US)

(73) Assignee: Celanese International Corporation, Dallas, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/470,360

(22) Filed: Dec. 22, 1999

(65) Prior Publication Data

US 2003/0013908 A1 Jan. 16, 2003

(51) Int. Cl.[7] .................. C07C 69/74; C07C 69/76; C07C 69/52
(52) U.S. Cl. ................ 560/265; 560/91; 560/205
(58) Field of Search .................. 560/205, 91, 265

(56) References Cited

U.S. PATENT DOCUMENTS

| | | | | |
|---|---|---|---|---|
| 4,250,328 A | * | 2/1981 | Fujita et al. | 560/205 |
| 4,452,969 A | * | 6/1984 | McCready | 528/279 |
| 4,780,527 A | * | 10/1988 | Tong et al. | 528/279 |
| 4,868,329 A | * | 9/1989 | Powanda et al. | 560/205 |
| 5,231,222 A | * | 7/1993 | Papa et al. | 560/265 |
| 5,248,427 A | * | 9/1993 | Spiske et al. | 210/640 |
| 5,502,240 A | * | 3/1996 | Pugach et al. | 560/99 |

FOREIGN PATENT DOCUMENTS

| | | | |
|---|---|---|---|
| EP | 0 521 488 B1 | 1/1996 | .......... C07C/67/08 |
| GB | 1173089 | 3/1969 | |
| GB | 1 262 645 | 3/1969 | |

* cited by examiner

Primary Examiner—Ba K. Trinh
Assistant Examiner—Taylor V Oh
(74) Attorney, Agent, or Firm—M. Susan Spiering

(57) ABSTRACT

Disclosed herein is an improved process for producing ethyl acetate comprising contacting acetic acid and ethanol in a reaction zone in the presence of an acid catalyst, distilling formed vapors and condensing to form an organic phase rich in ethyl acetate and an aqueous phase rich in water, separating the phases and further distilling each phase to obtain a final purified ethyl acetate product and a water stream low in organic components, the improvement comprising directing the organic phase from the first distillation to the reaction zone. An alternate embodiment involves directing at least a portion of the organic phase from the first distillation to a membrane separation unit which removes water and/or alcohol from the organic phase rich in ethyl acetate.

6 Claims, 1 Drawing Sheet

PROCESS IMPROVEMENT FOR CONTINUOUS ETHYL ACETATE PRODUCTION

FIELD OF THE INVENTION

This invention relates to an improvement in the process for producing ethyl acetate and more particularly to the optimal placement of recycle streams and the use of a membrane separation unit to remove water from the resultant product stream.

BACKGROUND OF THE INVENTION

Methods for producing a product ester by the esterification of a lower carboxylic acid with an alcohol in the presence of an esterification catalyst are well known in the art, see for example U.S. Pat. No. 5,231,222 and British Patents 1,173,089 and 1,262,645.

Ethyl acetate is produced first, by reaction over a strong acid catalyst. Second, the resulting vapors are passed through a distillation zone, then cooled and condensed, and then distilled a second time to provide ethyl acetate with few impurities.

In conventional production processes, a portion of the produced product (with or without some impurities) is used as an azeotropic agent in the initial reaction vessel.

Esterification conventionally is performed at the base of a distillation column or in a separate reactor. In the typical reaction zone an alcohol containing from 2 to 5 carbon atoms is reacted with a carboxylic acid containing from 1 to 4 carbon atoms in the presence of an esterification catalyst. The product ester is recovered using phase separation from a product ester-water azeotrope, see for example, European Patent EP 0521 488 B1 issued to Union Carbide. This patent describes the typical preparation of higher esters than ethyl acetate, but the same process is basically used.

Although any esterification reaction produces a mole of water per mole of ester, the needs of the distillation which removes the ester from the reaction zone as an azeotrope with water vary according to what ester is being produced. In the case of ethyl acetate, there is too much water produced in the reaction to match the water-ester azeotrope. In the production of other esters, butyl acetate for example, too little water is produced in the reaction to match the azeotrope. Adjusting this water to ester ratio in the distillation is important for economical production of the ester.

The table below illustrates examples of the differences between the stoichiometric water produced and the azeotropic composition.

TABLE A

| Acetate | Differences between Stoichiometric and Azeotropic Water Composition | |
|---|---|---|
|  | Stoich. | Azeotrope |
| ESTER | % WATER | |
| Methyl | 19.5% | 3.2% |
| Ethyl | 17.0% | 8.7% |
| i-Propyl | 15.0% | 10.5% |
| n-Propyl | 15.0% | 14.0% |
| n-Butyl | 13.4% | 28.7% |
| i-Butyl | 13.4% | 16.5% |
| s-Butyl | 13.4% | 22.5% |

TABLE A-continued

| Acetate | Differences between Stoichiometric and Azeotropic Water Composition | |
|---|---|---|
|  | Stoich. | Azeotrope |
| PROPIONATE | | |
| Methyl | 17.0% | 8.2% |
| Ethyl | 15.0% | 10.0% |
| i-Propyl | 13.4% | 19.9% |
| n-Propyl | 13.4% | 23.0% |
| BUTYRATE | | |
| Methyl | 15.0% | 11.5% |
| Ethyl | 13.4% | 21.5% |
| ISO-BUTYRATE | | |
| Methyl | 15.0% | 6.8% |
| Ethyl | 13.4% | 15.2% |
| ACRYLATE | | |
| Methyl | 17.3% | 7.2% |
| Ethyl | 15.2% | 15.0% |
| METHACRYLATE | | |
| Methyl | 15.2% | 14.0% |

Ref: Advances in Chemistry Series, 116, Azeotropic Data III, ACS, Washington, D.C., 1973.

For those esters which produce more water than the azeotrope will remove, an azeotropic agent must be added. For those situations, the present invention applies.

Control of the amount of water in the process, and critical introduction of water into various stages of the production process for ethyl acetate are has been a constant issue. The present invention is directed to a method for controlling water in the production process to provide an optimized production process. Further the invention is directed to points at which water can be removed from the production process to debottleneck the process.

Additionally, the present invention is directed to a method for control of the amount of resulting acid from the final ethyl acetate product, wherein the amount of acid present in the final product is less than about 50 ppm acetic acid.

SUMMARY OF THE INVENTION

Disclosed is an improved process to produce ethyl acetate, which contains minor amounts of acetic acid, typically less than about 50 ppm. Additionally, a process is disclosed for producing ethyl acetate by using an additional step to remove a substantial amount of water from a condensed reaction stream and recycling portions of that dried stream back into the production process. Another portion of the dried stream is processed in a second distillation zone to produce an ethyl acetate product.

More particularly, an improved process for producing ethyl acetate is disclosed comprising contacting acetic acid and ethanol in a reaction zone in the presence of an acid catalyst, distilling the formed vapors and condensing to form an organic phase rich in ethyl acetate and an aqueous phase rich in water, separating the phases and further distilling each phase to obtain a final purified ethyl acetate product and a water stream low in organic components, the improvement comprising directing at least a portion of the organic phase from the first distillation to the reaction zone.

An alternate embodiment of the present invention involves directing at least a portion of the organic phase from the first distillation to a membrane separation unit which removes water, alcohol, or a combination of water and alcohol from the organic phase rich in ethyl acetate

DETAILED DESCRIPTION OF THE INVENTION

Figure 1:
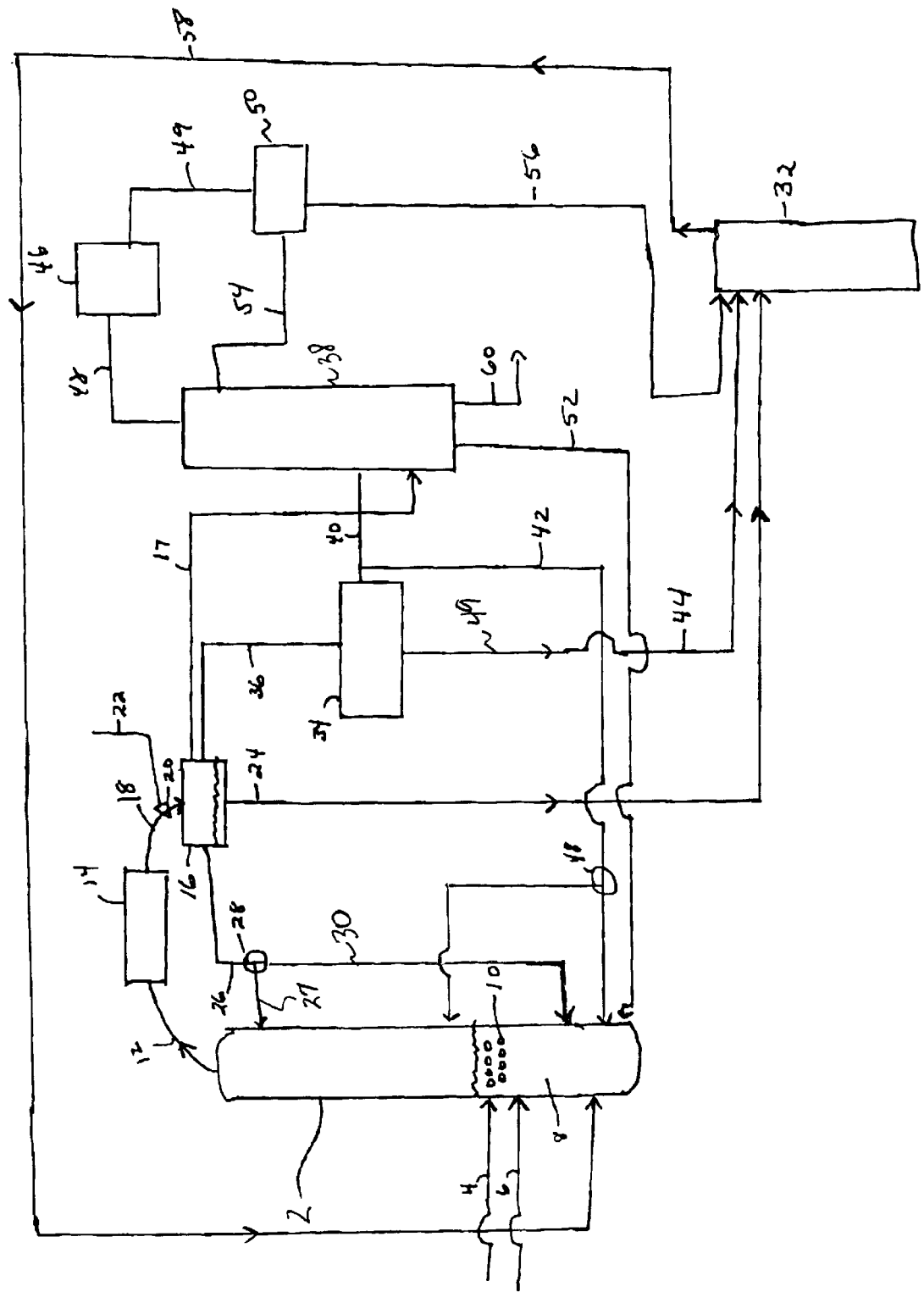
FIG. 1 illustrates a flow diagram embodiment of the esterification process of this invention.

In accordance with this invention, there are provided various alternatives for improving the capacity of an ethyl acetate manufacturing process. More specifically, the invention is related to the removal of water from the esterification reaction zone.

The invention relates to the known esterification processes for producing a product ester, wherein an alcohol containing from 2 to 5 carbon atoms is reacted with a carboxylic acid containing from 1 to 4 carbon atoms. Conventional esterification techniques and processes may be employed with the present invention. Specific reaction parameters vary based on equipment and artisans will recognize which parameters to utilize. Reaction conditions and processing techniques may be varied to meet individual needs, the conditions surrounding the processing plant, and the particular ester product desired.

Exemplary product esters of the present invention include those of the formula

RCOOR' where R represents 1 to 4 carbon atoms and wherein R' represents an alkyl radical having from 2 to 5 carbon atoms and preferably those esters that do not produce too much water for the azeotrope. Illustrative product esters include ethyl acetate, n-propyl acetate, iso-propyl acetate, ethyl propionate, methyl iso-butyrate, and the like. The preferred product ester of this invention is ethyl acetate. The present invention will thus be described relative to the preferred ester, i.e., ethyl acetate. Those of skill in the art will recognize that the description is applicable to other esters. The description and examples herein are not intended to limit the scope of the invention.

Exemplary carboxylic acid starting materials employed in the present invention include those of the formula

RCOOH wherein R represents 1 to 4 carbon atoms. Illustrative carboxylic acids include acetic acid, propionic acid and butyric acid. The preferred carboxylic acid starting material is acetic acid. Most preferably, the carboxylic acid starting materials are purified single carboxylic acids, although mixtures of such acids could be employed if desired.

Exemplary alcohol starting materials of in this invention are those with the formula

R'OH wherein R' represents an alkyl radical having from 2 to 5 carbon atoms. Illustrative alcohols include ethanol, n-propanol, isopropanol, n-butanol, isobutanol, sec-butanol, amyl alcohols such as 1-pentanol and mixtures thereof, and the like. The preferred alcohol is ethanol for use in the present invention. It is of course to be understood that while it is more preferred to employ purified single alcohol starting materials, mixtures of alcohols, may be employed if desired.

As shown in FIG. 1, ethyl acetate is typically produced by a series of steps employing a reaction/distillation tower 2 and two feed streams, an acetic acid feed stream 4 and an ethanol feed stream 6. In accordance with the present invention, both feed streams are introduced at the bottom of the reaction/distillation tower 2, where the reaction zone 8 is located. The feed streams are passed into the reaction zone 8, which generally contains a catalyst. The catalyst can be in the form of a packed bed 10 or alternatively, a soluble strong ($pK_a$ generally less than about 1) acid to cause the necessary chemical reaction.

The esterification can be operated under batch or continuous mode. For commercial purposes, continuous operation is preferred. Illustrated in FIG. 1 is a continuous production process. The continuous process utilizes a corrosion resistant reaction/distillation tower 2, constructed from a material, such as 316 stainless steel. Feed flows continuously through reaction zone 8. Material simultaneously leaves the reaction zone as a vapor and enters the bottom of the distillation zone. Typically for ethyl acetate production, the reaction zone is maintained at temperatures in the range of about 70° C. to about 145° C., at pressures of atmospheric to about 3 atmospheres absolute. One of skill in the art will recognize that various temperatures can be used depending on the pressure maintained in the reaction zone 8, and the specific ester being produced and nature of materials.

Typically the alcohol and acid are fed in equimolar amounts. In commercial practice, the reaction/distillation tower is fed a slight excess of alcohol. This excess is supplied by recycled alcohol from the finishing and recovery towers 38 and 32 respectively.

In the reaction zone 8, at the base of the tower 2, is preferably located a strong acid catalyst to initiate the reaction. A variety of homogeneous or heterogeneous acids can be employed within the scope of this invention. Alkyl sulfonic acids and aromatic sulfonic acids are usable herein. Exemplary acids include, without limitation sulfonic acids, such as methane sulfonic acid, benzene sulfonic acid, and p-toluene sulfonic acid. Alternatively, sulfuric acid or heteropoly acids can be used within the scope of this invention. A strong acid ion exchange resin such as Rohm and Haas A-16 can be used in the reaction zone of this invention. The esterification catalyst is employed in an amount sufficient to initiate and maintain reaction. A homogeneous catalyst liquid phase or a pump around bed, which enable the liquid to be pumped across a packed bed of solid catalyst can be employed within the scope of the present invention.

In an embodiment of the invention, the base temperature in the distillation tower is about 117° C. in a 45 tray distillation tower. The overhead temperature is about 93° C. at about 2.1 atmospheres absolute. The resulting vapor, which is pulled off the top of the tower, is typically comprised of ethyl acetate, water, slight amounts of ethanol and acetic acid. At this point, the acetic acid content is considerably less than the ethanol content in the stream.

The reaction/distillation tower 2 generally should contain at least about 35–70 trays, with 45–55 trays being preferred. The key separation being done in this tower is the removal of acetic acid from the distillate product. It has been found that about 35–70 trays is necessary to accomplish the separation of acetic acid from ethyl acetate and distillate.

After reaction and distillation, the resulting vapors are removed from the top of the tower 2 via line 12 to a condenser 14, such as an air cooled condenser. Other types of condensers may be employed. For example, a process to process exchanger could be used as a condenser. The vapors may also be condensed using refrigeration. When condensation occurs, two liquid phases form. The lower density or lighter phase is an organic phase rich in ethyl acetate. The more dense, or heavier phase, is an aqueous phase rich in water. Better separation of the phases occurs with lower temperatures.

As shown in FIG. 1, condenser 14 is then connected to a phase separator or decanter 16. The condenser 14 and decanter 16 are connected by line 18. Water can be added via line 22 at water addition port 20 to stream 18 to enhance phase separation in decanter 16.

After decanting, an aqueous phase is removed off the bottom of the decanter 16 via line 24. A portion of the organic phase from decanter 16 is passed through line 26 back to the top of tower 2 as reflux 27. Alternatively the reflux of line 26 can be split at splitter 28 and the reflux of line 26 can flow both to the top of tower 2 via line 27, and to the reaction zone 8 via line 30. A portion can also be passed by line 17 to finishing column 38. The use of line 30 in this manner decreases liquid load on the trays of the reaction/distillation tower 2, while still providing the necessary azeotroping agent to the reaction zone. The aqueous phase from decanter 16 is forwarded via line 24 to an organic recovery column or tower 32.

A portion of the organic phase of decanter 16 is passed to a membrane separation unit, or a pervap unit 34 via line 36. The membrane separation unit or pervap unit may be employed to remove the water or alcohol present in the product ester. The membrane separation or pervap unit 34 is a unit which was developed on the concepts of "permeation" and "evaporation." These units are well known to those skilled in the art and are available from, among others, Sulzer Chemtech GmbH and Artisan Industries, Inc.

Using a membrane separation unit in this manner represents an improvement over the known art. The advantage offered is an alternative method of removing water from the reaction system. The dried organic stream can then be either processed further to produce pure ethyl acetate in the finishing column 38, or this dried stream can be used as an azeotroping agent in distillation tower 2. The pervap unit thus removes additional water and/or alcohol from the ethyl acetate stream, enabling debottlenecking of the subsequent finishing column.

The treated pervap unit stream can be passed either to the finishing column 38 by line 40, to or passed back to the tower 2 so that the ethyl acetate portion of the stream can act as an azeotropic agent for the reaction/distillation tower 2 via line 42. Alternatively, stream 40 can go to both the finishing column 38 and the reaction zone 8. The flow to reaction zone 8 is via line 42 which can be split again via splitter 48 so that a portion, e.g. line 49, of stream 42 can be introduced at the lower third of the distillation zone of tower 2 along with, or independently of, the introduction of flow 42 into reaction zone 8. Additionally, stream 44 can be passed from the pervap unit 34 to the organic recovery column 32.

The second distillation zone 38, also referred to as the finishing tower, is preferably operated at a pressure of about 1 to about 4 atmospheres absolute. The second distillation zone preferably contains about 25–50 trays, more preferably about 30–50 trays. The key separation is the removal of ethanol and water from the product ethyl acetate.

After entering the finishing column 38, vapors once again pass out the top of the column to a second condenser 46 via line 48. After condensing, the condensate can be passed via line 49 to a decanter 50.

Decanter 50 separates the condensate into two flows. Stream 54 is an organic phase which provides reflux to the top of column 38. Stream 56 is an aqueous stream which passes to the organic recovery tower 32.

A portion of the residue from the finishing tower 38 may pass to the reaction zone 8 via stream 52. The ethyl acetate in this stream enhances the separation in the tower 2 by satisfying the water/ethyl acetate azeotrope. If adequate azeotroping agent is fed to the distillation tower 2, by lines 26 and 42, no flow is required through stream 52.

Both decanters 50 and 16 are operated as cold as possible, preferably at temperatures from a refrigerated 5° C. to about 50° C. so that very good separation occurs between the organic (ethyl acetate) and the aqueous phase.

With the installation of the pervap unit 34, this production process no longer needs to utilize the on-specification essentially pure ethyl acetate in the reaction/distillation column 2. Instead, a less pure stream containing ethyl acetate can be used as the azeotropic agent, thereby increasing the capacity of the finishing column 38 to produce on-specification product without a bottleneck due to removal of the water from the decanted stream from the reaction/distillation column.

Product is pulled off the bottom of finishing column 38 via line 60. This finished product, ethyl acetate, contains less than about 0.5% total impurities, and specifically contains less than about 50 ppm acetic acid.

EXAMPLE

A reaction/distillation column consisting of 45 sieve trays received two feed streams, ethanol and acetic acid. Both feed streams were introduced at the bottom of the reaction vessel i.e. the reaction zone. The unit (reaction, finishing, and recovery towers) received essentially a 1:1 molar ratio of feeds. Due to the recycles from the recovery tower, the reaction zone received a slight excess of alcohol. Methane sulfonic acid, as catalyst, was used to react the feed streams. The reaction products leave the reaction zone as and create a vaporous ethyl acetate, ethanol, acetic acid and water mixture. The vaporous mixture rises in the column, and distillation occurs. The distillation portion of the column was operated at an overhead pressure of about 2 atmospheres absolute with an overhead temperature of about 93° C. The resulting vapors passed through an air cooled condenser. Water was introduced into the outlet line from the condenser to improve phase separation. The added water decreases the alcohol content of the aqueous and organic phases. Decreasing the alcohol content of the organic phase has two benefits:

1. The organic phase carries less alcohol to the finishing column and thus increases its capacity to produce specification product, and
2. lowering the alcohol content of the organic phase also lowers the solubility of water in that phase, causes less water to be fed to both the reaction/distillation column and the finishing column, and adds to the capacity increase by further decreasing the vapor load on that column.

The condensed material was then separated into an organic phase rich in ethyl acetate and an aqueous phase rich in water, but also containing some ethanol and ethyl acetate. The separation occurred via a decanter or phase separator. The aqueous phase was then forwarded to an organic recovery column. The ethyl acetate stream is further separated into a first stream that flows to the top of the reaction/distillation column, a second stream that flows directly to a finishing column, and a third stream that flows to a membrane separation unit. A fourth stream or a portion thereof can also be fed to the reaction zone in the bottom of the reaction/distillation column to add ethyl acetate to the zone to assist in the water removal.

The stream that is transmitted to the membrane separation unit is then treated, creating two more streams. The permeate can be added to the aqueous phase coming from the first decanter which flows to an organic recovery column to allow recovery and reuse of valuable ethanol and ethyl acetate dissolved in the aqueous stream. The other stream, i.e., the dehydrated organic stream from the membrane separation unit can be added directly to the reaction zone in the reaction/distillation column, thereby providing an azeotropic agent, which has not been subjected to the extensive purification of the finishing column, thereby lowering the cost of the azeotropic agent used in current commercial processes.

To recover any alcohol remaining in the crude ethyl acetate streams (reaction tower distillate organic phase and product from membrane separation unit), these organic streams are fractionally distilled, with the essentially pure product being taken from off the bottom of the finishing column and the vapor is passed to a condenser which then cools the stream and passes the material to a phase separator, wherein the ethanol can be recovered from the aqueous phase from the bottom of the separator, and the organic phase is recycled to the reaction zone.

We claim:

1. A process for producing ethyl acetate comprising:
   (a) reacting acetic acid and ethanol in a reaction zone;
   (b) directing vapors formed in the reaction zone to a distillation means to form an azeotrope containing 10 wt. % or less of water;
   (c) condensing the azeotrope to form a condensate;
   (d) separating the condensate into an organic phase rich in ethyl acetate and an aqueous phase rich in water; and
   (e) directing at least a portion of the organic phase rich in ethyl acetate to the reaction zone as an azeotroping agent.

2. The process of claim 1 wherein at least a portion of the organic phase is directed to a membrane separation unit to form a dried organic stream.

3. The process of claim 2 wherein at least a portion of the dried organic stream is directed to the distillation means.

4. The process of claim 3 wherein at least a portion of the dried organic stream is directed to the reaction zone.

5. A process for producing ethyl acetate comprising:
   (a) reacting acetic acid and ethanol in a reaction zone;
   (b) directing vapors formed in the reaction zone to a distillation means to form an azeotrope containing 10 wt. % or less of water;
   (c) condensing the azeotrope to form an condensate;
   (d) separating the condensate into an organic phase rich in ethyl acetate and an aqueous phase rich in water; and
   (e) directing at least a portion of the organic phase rich in ethyl acetate to a membrane separation unit to form a dried organic stream; and
   (f) directing at least a portion of the dried organic stream to the distillation means as an azeotroping agent.

6. The process according to claim 5 wherein at least a portion of the dried organic stream is directed to the reaction zone.

* * * * *